United States Patent
Ito et al.

(10) Patent No.: US 6,737,666 B1
(45) Date of Patent: May 18, 2004

(54) APPARATUS AND METHOD FOR DETECTING AN END POINT OF A CLEANING PROCESS

(75) Inventors: Natsuko Ito, Tokyo (JP); Tsuyoshi Moriya, Tokyo (JP); Fumihiko Uesugi, Tokyo (JP); Yoshinori Kato, Yamanashi (JP); Masaru Aomori, Yamanashi (JP); Shuji Moriya, Yamanashi (JP); Mitsuhiro Tachibana, Yamanashi (JP)

(73) Assignees: NEC Electronics Corporation, Kanagawa (JP); Tokyo Electron Limited, Tokyo (JP)

( * ) Notice: Subject to any disclaimer, the term of this patent is extended or adjusted under 35 U.S.C. 154(b) by 100 days.

(21) Appl. No.: 09/721,703

(22) Filed: Nov. 27, 2000

(30) Foreign Application Priority Data

Nov. 26, 1999 (JP) .......................... 11-336432

(51) Int. Cl.[7] .......................... G01N 21/49; H01L 21/66
(52) U.S. Cl. .......................... 250/574; 438/16; 438/905; 438/14
(58) Field of Search .......................... 250/573, 574, 250/576; 438/477, 905, 14, 15, 16; 34/359, 524, 529, 85

(56) References Cited

U.S. PATENT DOCUMENTS

| | | | | |
|---|---|---|---|---|
| 5,815,264 A | * | 9/1998 | Reed et al. | 356/336 |
| 6,060,397 A | * | 5/2000 | Seamons et al. | 438/694 |
| 6,122,042 A | * | 9/2000 | Wunderman et al. | 356/73 |

FOREIGN PATENT DOCUMENTS

| JP | 61-256637 | 11/1986 |
|---|---|---|
| JP | 63-5532 | 1/1988 |
| JP | 63-14421 | 1/1988 |
| JP | 63-89684 | 4/1988 |
| JP | 63-128718 | 6/1988 |
| JP | 63-129629 | 6/1988 |
| JP | 06-224163 | 8/1994 |
| JP | 07-169753 | 7/1995 |
| JP | 07-179641 | 7/1995 |
| JP | 08-306628 | 11/1996 |
| JP | 09-143742 | 6/1997 |
| JP | 09-260358 | 10/1997 |
| JP | 10-55966 | 2/1998 |
| JP | 10-163116 | 6/1998 |
| JP | 10232196 | 9/1998 |
| JP | 11-87248 | 3/1999 |
| JP | 11-131211 | 5/1999 |

* cited by examiner

*Primary Examiner*—David Porta
*Assistant Examiner*—David C Meyer
(74) *Attorney, Agent, or Firm*—Sughrue Mion, PLLC

(57) ABSTRACT

A cleaning end point detecting apparatus detects an end point of a cleaning process in which contamination attached to an inner wall of a reaction chamber is removed by introducing a cleaning gas into the chamber to produce a cluster cloud and detached particles. An irradiating unit irradiates a laser beam onto the cluster cloud and the detached particles within the reaction chamber to produce a scattered laser beam. A monitoring unit monitors the scattered laser beam as a two-dimensional image information. A judging unit judges the end point of the cleaning process on the basis of the two-dimensional image information. Preferably, the judging unit judges, as the end point of the cleaning process, a time instant when neither the detached particles nor the cluster cloud are detected on the basis of the two-dimensional image information.

8 Claims, 4 Drawing Sheets

APPARATUS AND METHOD FOR DETECTING AN END POINT OF A CLEANING PROCESS

BACKGROUND OF THE INVENTION

This invention relates to a method and an apparatus for detecting an end point of a dry cleaning process for removing unnecessary substances deposited in an apparatus for producing a semiconductor device.

An apparatus for producing a semiconductor device has a vacuum chamber in which a process gas is activated by heat or plasma to process a semiconductor substrate. After the semiconductor substrate is processed, unnecessary substances including reaction products and deposits are attached to an inner wall of the vacuum chamber as a contamination. Therefore, the vacuum chamber requires a cleaning process in order to remove the contamination. If an operator opens the vacuum chamber and manually removes the contamination, the temperature and/or the pressure in the vacuum chamber must be changed from processing conditions into normal conditions to allow the entrance of the operator. After completion of the cleaning process, the temperature and the pressure in the vacuum chamber must be recovered into the processing conditions to start a next process. This requires a long time and therefore decreases a productivity.

In view of the above, use is generally made of a cleaning method using a cleaning gas. Specifically, the cleaning gas is introduced into the vacuum chamber and activated by the heat or the plasma. The cleaning gas thus activated reacts with the contamination to thereby remove the contamination.

Traditionally, it is assumed that the cleaning process is completed at a time instant after the lapse of a predetermined cleaning time period which is experientially determined through visual observation by the operator.

In case where the cleaning process is carried out by the use of the plasma, the completion of the cleaning process can be detected by monitoring the change in plasma emission spectrum. Such technique is disclosed, for example, in Japanese Unexamined Patent Publications (JP-A) Nos. S63-005532, S63-014421, S63-089684, and H07-169753. This technique makes use of the fact that the plasma emission spectrum observed during the reaction between the contamination and the cleaning gas is different from that observed after the contamination is removed through the reaction.

Alternatively, the completion of the cleaning process may be detected by monitoring the change in pressure within the vacuum chamber. This technique is disclosed, for example, in Japanese Unexamined Patent Publications (JP-A) Nos. S63-129629, H06-224163, H09-143742, and H11-131211. This technique makes use of the fact that the pressure during the reaction between the contamination and the cleaning gas Is different from that in presence of the cleaning gas alone. Specifically, when the cleaning process is started, the pressure in the vacuum chamber increases because the cleaning gas reacts with the contamination to produce a resultant gas. The pressure continuously increases with the progress of the reaction between the cleaning gas and the contamination and, when the contamination is reduced in amount and the reaction is weakened, decreases to gradually approach a predetermined level. The time instant when the pressure reaches the predetermined level is detected as a cleaning end point.

In Japanese Unexamined Patent Publications (JP-A) Nos. H09-260358 and H11-087248, disclosure is made of a technique of detecting the cleaning end point by the use of a particle counter arranged in a discharge line from the vacuum chamber to monitor the contamination detached from the Inner wall of the vacuum chamber as particles. The particle counter comprises a counter capable of counting the number of particles having a diameter of 0.2 $\mu$m or more. Every time when a preselected cleaning time period has lapsed, a nitrogen purging is carried out and the number of particles contained in a discharge gas is counted. When the number of particles is decreased to a preselected level or less, the completion of the cleaning process is judged.

Alternatively, use may be made of techniques utilizing the changes in high-frequency voltage, electric potential of a substrate being processed, and plasma impedance. For example, Japanese Unexamined Patent Publication (JP-A) No. S61-256637 discloses the technique of detecting the end point in response to the change in high-frequency voltage. Japanese Unexamined Patent Publication (JP-A) No. S63-128718 discloses the technique of detecting the end point in response to the change in electric potential of the substrate being processed. Japanese Unexamined Patent Publication (JP-A) No. H07-179641 discloses the technique of detecting the end point in response to the change in plasma impedance.

On the other hand, in a thermal processing apparatus which does not use the plasma, the end point of the cleaning process may be detected by a technique of monitoring the temperature within the vacuum chamber. Such technique is disclosed, for example, in Japanese Unexamined Patent Publications (JP-A) Nos. H8-0306628, H10-055966 and H10-163116. Specifically, reaction heat produced during the reaction between the contamination and the cleaning gas is monitored.

In the above-mentioned conventional techniques, however, it is difficult to accurately detect the end point of the cleaning process. Hereinafter, various problems in the conventional techniques will be described.

In the technique of finishing the cleaning process at the time instant after the lapse of the predetermined cleaning time period experientially determined, incomplete cleaning may often be caused. This is because a cleaning time period actually required before the end point of the cleaning process is variable. For example, the amount of the contamination may be changed in dependence upon process conditions. The cleaning time period for complete cleaning may be changed in dependence upon cleaning conditions. In order to avoid the incomplete cleaning, the predetermined cleaning time period must be prolonged. This results in decrease in operation rate of the apparatus and increase in consumption of the cleaning gas.

In the technique of detecting the end point of the cleaning process by monitoring the change in plasma emission spectrum, plasma emission around the center of the vacuum chamber is monitored. It is difficult to monitor the plasma emission caused by the reaction in the vicinity of the inner wall of the vacuum chamber. Therefore, the end point of the cleaning process is often detected erroneously. In addition, this technique is not applicable to a thermal CVD (Chemical Vapor Deposition) process which does not use the plasma.

The technique of monitoring the change in pressure within the vacuum chamber is disadvantageous in the following respect. The contamination partially reacts with the cleaning gas to produce a resultant gas and partially detached from the inner wall as particles because the adhesion strength is weak. The particles are discharged together with the cleaning gas. Therefore, in dependence upon the amount of the part discharged as the particles, the convergence time of the pressure within the vacuum chamber will be varied. This deteriorates the repeatability in detecting the end point of the cleaning process. As compared with the pressure within the vacuum chamber, the change in pressure is so small that the measurement is difficult.

In the technique of counting the number of particles in the discharge line from the vacuum chamber, it is often necessary to repeat the cleaning process and the counting operation of counting the number of particles during the nitrogen purging a plurality of times. In particular, in order to accurately detect the end point of the cleaning process, the cleaning time period is shortened and the counting operation is frequently carried out. Thus, the detection of the end point with this technique is requires a long time and an increased number of steps.

In the techniques utilizing the changes in high-frequency voltage, electric potential of the substrate being processed, and plasma impedance during the cleaning process using the plasma, the change in strength of such electric signal is so small that the stability or the reliability in detection of the end point of the cleaning process is low.

The technique of monitoring the reaction heat produced during the reaction between the contamination and the cleaning gas is mainly used in the thermal process which does not use the plasma. However, as compared with an atmospheric temperature within the vacuum chamber, the reaction heat is so small that the stability or the reliability in detecting the end point. of the cleaning process is low. Furthermore, the relationship between the end point of the cleaning process and a temperature drop time period required before a desired temperature is reached is not constant. Therefore, it is impossible to detect the end point of the cleaning process with high accuracy and excellent repeatability.

SUMMARY OF THE INVENTION

It is therefore an object of this invention to provide a cleaning end point detecting apparatus which is capable of accurately detecting an end point of a cleaning process.

It is another object of this invention to provide a cleaning end point detecting method which is capable of accurately detecting an end point of a cleaning process.

According to this invention, there is provided a cleaning end point detecting apparatus for detecting an end point of a cleaning process in which contamination attached to an inner wall of a reaction chamber is removed by introducing a cleaning gas into the reaction chamber to produce within the reaction chamber a cluster cloud resulting from reacting a part of the contamination with the cleaning gas and to detach the other part of the contamination from the inner wall as detached particles and by discharging the cluster cloud and the detached particles from the reaction chamber together with the cleaning gas, the apparatus comprising:

irradiating means for irradiating a laser beam onto the cluster cloud and the detached particles within the reaction chamber to produce a scattered laser beam scattered by the cluster cloud and the detached particles;

monitoring means for monitoring the scattered laser beam as a two-dimensional image information; and judging means for judging the end point of the cleaning process on the basis of the two-dimensional image information.

According to this invention, there is also provided a cleaning end point detection method of detecting an end point of a cleaning process in which contamination attached to an inner wall of a reaction chamber is removed by introducing a cleaning gas into the reaction chamber to produce within the reaction chamber a cluster cloud resulting from reacting a part of the contamination with the cleaning gas and to detach the other part of the contamination from the inner wall as detached particles and by discharging the cluster cloud and the detached particles from the reaction chamber together with the cleaning gas, the method comprising the steps of:

irradiating a laser beam onto the cluster cloud and the detached particles within the reaction chamber to produce a scattered laser beam scattered by the cluster cloud and the detached particles;

monitoring the scattered laser beam as a two-dimensional image information; and judging the end point of the cleaning process on the basis of the two-dimensional image information.

In the cleaning process, a part of the contamination reacts with the cleaning gas to produce a reaction product gas. The reaction product gas reacts in a vapor phase to produce the cluster cloud. As a result of production of the cluster cloud, the other part of the contamination is weakened in adhesion strength to be detached from the inner wall as the detached particles. The detached particles are greater in particle size than the cluster cloud. A test region including the cluster cloud and the detached particles is irradiated by the laser beam to monitor the detached particles and the cluster cloud by a laser beam scattering technique. When the detached particles and the cluster cloud are no longer observed because of exhaustion of the contamination, it is judged that the end point of the cleaning process is reached.

DESCRIPTION OF PREFERRED EMBODIMENTS

Figure 1:
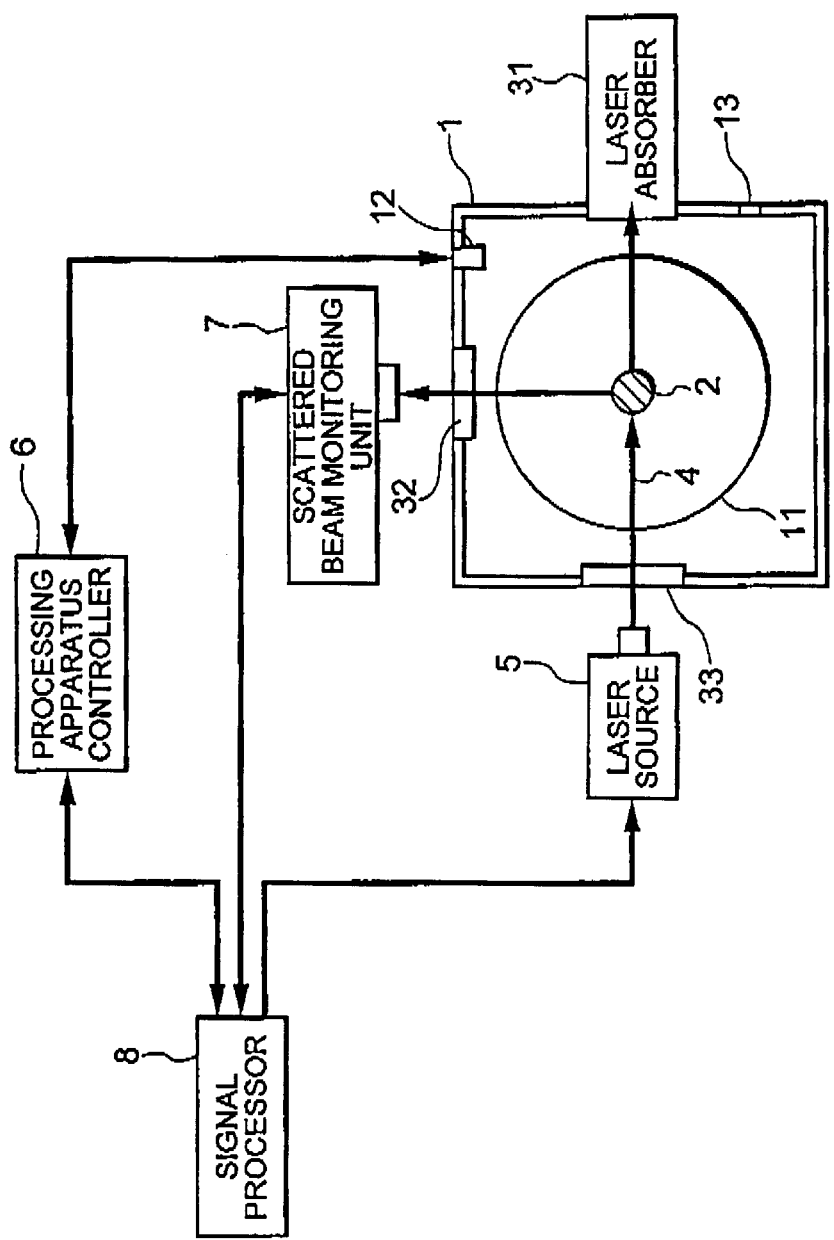
FIG. 1 is a view showing a cleaning end point detecting apparatus according this invention.

Now, this invention will be described with reference to the drawing.

Referring to FIG. 1, a cleaning end point detecting apparatus according to this invention is for detecting an end point of a cleaning process for removing a contamination attached to an inner wall of a reaction chamber (processing chamber) 1 of a processing apparatus and a wafer support 11 arranged in the reaction chamber 1.

The cleaning process is carried out in the following manner under control of a processing apparatus controller 6. Specifically, a cleaning gas is introduced into the reaction chamber 1 through a gas inlet port 12. Through the reaction between a part of the contamination and the cleaning gas, a cluster cloud is produced in the reaction chamber 1. Simultaneously, the other part of the contamination is detached from the inner wall and the wafer support 11 as detached particles. The cluster cloud and the detached particles are discharged from the reaction chamber 1 through a discharge port 13 together with the cleaning gas. Thus, the contamination attached to the inner wall of the reaction chamber 1 and the wafer support 11 is removed.

In order to detect the end point of the above-mentioned cleaning process, the cleaning end point detecting apparatus of this invention comprises a laser source 5, a scattered beam monitoring unit (or a scattered beam measuring unit) 7, and a signal processor 8.

The laser source 5 is for irradiating a laser beam 4 through a laser beam incident window 33 onto the cluster cloud and the detached particles 2 within the reaction chamber 1 to produce a scattered laser beam scattered by the cluster cloud and the detached particles 2. The scattered laser beam passes through a scattered beam monitoring window 32 of the reaction chamber 1 to be incident to the scattered beam monitoring (or measuring) unit 7. On the other hand, the laser beam 4 emitted from the laser source 5 passes through the reaction chamber 1 to be absorbed by a laser absorber 31 fixed to the reaction chamber 1.

The scattered beam monitoring (or measuring) unit 7 serves to monitor the scattered laser beam passing through the scattered beam monitoring window 32 as two-dimensional image information. Typically, the scattered beam monitoring (or measuring) unit 7 comprises a CCD (Charge Coupled Device) camera.

The signal processor 8 is responsive to the two-dimensional image information supplied from the scattered beam monitoring (or measuring) unit 7 and operates as an end point detector for detecting the end point of the cleaning process.

Specifically, the signal processor (end point detector) 8 is supplied with the two-dimensional image information from the scattered beam monitoring (or measuring) unit 7 and detects, as the end point of the cleaning process, a time instant when not only the detached particles but also the cluster cloud is no longer detected.

More in detail, the signal processor (end point detector) 8 is responsive to the two-dimensional image information and detects, as the end point of the cleaning process, a time instant when the density of the particles having a predetermined size is decreased to a predetermined density. The predetermined size is substantially equal to the particle size of the cluster cloud and, for example, not greater than 20 nm. In this event, the predetermined density is equal to, for example, 100 /cm$^2$.

First Embodiment

Referring to FIG. 1, a first embodiment of this invention will be described.

The laser beam 4 is introduced through the laser beam incident window 33 into the reaction chamber (vacuum chamber) 1 of a tungsten thermal CVD apparatus as the processing apparatus. The scattered laser beam by the cluster cloud and the detached particles 2 is monitored by the scattered beam monitoring (or measuring) unit 7 as a two-dimensional image. As the laser beam 4, use is made of a YAG laser (yttrium-aluminum-garnet) having a double wavelength of 532 nm and an average power of 2.5W. The scattered beam monitoring (or measuring) unit 7 may comprise a CCD camera responsive to the scattered laser beam for producing an Image signal corresponding to the strength of the scattered laser beam. The signal processor 8 is supplied with the image signal from the scattered beam monitoring (or measuring) unit 7 and an apparatus status signal and carries out image processing for the image signal supplied thereto.

Figure 2:
FIG. 2 is a view showing a monitored image obtained by a scattered beam monitoring unit of the cleaning end point detecting apparatus illustrated in FIG. 1.
Figure 3:
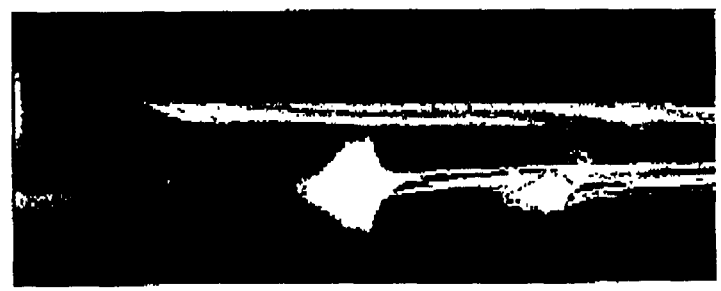
FIG. 3 is a view showing another monitored image similar to that illustrated in FIG. 2.

Referring to FIGS. 2 and 3, the scattered beam monitoring (or measuring) unit 7 monitors the two-dimensional image as exemplified in the figures. In FIG. 2, the laser beam 4 is shown at the center of the figure as a thin white line across a screen. The monitored image in FIG. 2 is acquired immediately after start of the cleaning process using ClF$_3$. In the monitored image, no detached particles are observed but the scattered beam is detected because of presence of a fine cluster cloud. With the progress of the cleaning process, the detached particles are detected as shown in FIG. 3. As compared with FIG. 2, the scattered beam is brightened and a large detached particle leaves a locus shown as a thick white line.

The signal processor 8 carries out image processing to obtain the intensity of the scattered beam from the detached particles and the cluster cloud and detects, as the end point of the cleaning process, a time instant when the intensity is converged. Then, the signal processor 8 produces an end point signal representative of the end point of the cleaning process and delivers the end point signal to the processing apparatus controller 6. Supplied with the end point signal, the processing apparatus controller 6 carries out a cleaning ending operation such as stop of the introduction of the cleaning gas into the reaction chamber 1.

Second Embodiment

Referring to FIG. 1 again, a second embodiment of this invention will be described.

This invention is also applicable to a plasma cleaning process of the tungsten thermal CVD apparatus as the processing apparatus by the use of NF$_3$.

The laser beam 4 is introduced through the laser beam incident window 33 into the reaction chamber (processing chamber) 1 of the thermal CVD apparatus. The scattered laser beam scattered by the cluster cloud and the detached particles 2 is monitored by the scattered beam monitoring (or measuring) unit 7 as the two-dimensional image.

In this case, plasma emission could be background light. Therefore, in order to efficiently monitor the scattered laser beam, the scattered beam monitoring (measuring) unit 7 is provided with a filter for transmitting the wavelength of the laser beam alone. The signal processor 8 receives the image signal from the scattered beam monitoring (or measuring) unit 7 and carries out image processing for the image signal supplied thereto.

In case of the plasma cleaning, the contamination detached from the inner wall of the vacuum chamber are not likely to enter the inside of the plasma. Therefore, the end point of the cleaning process can be accurately detected by monitoring the vicinity of the inner wall.

By the Image processing, the strength of the scattered laser beam scattered from the cluster cloud and the detached particles is obtained. The time instant when the strength is converged is detected as the end point of the cleaning process. The end point signal representative of the end point of the cleaning process is delivered to the processing apparatus controller 6. Supplied with the end point signal, the processing apparatus controller 6 carries out the cleaning ending operation such as stop of introduction of the cleaning gas into the reaction chamber 1.

In this invention, detection of the end point of the cleaning process can similarly be carried out for a different processing apparatus, such as a tungsten plasma etching apparatus, by the use of a different cleaning gas, such as ClF$_3$.

Third Embodiment

Figure 4:
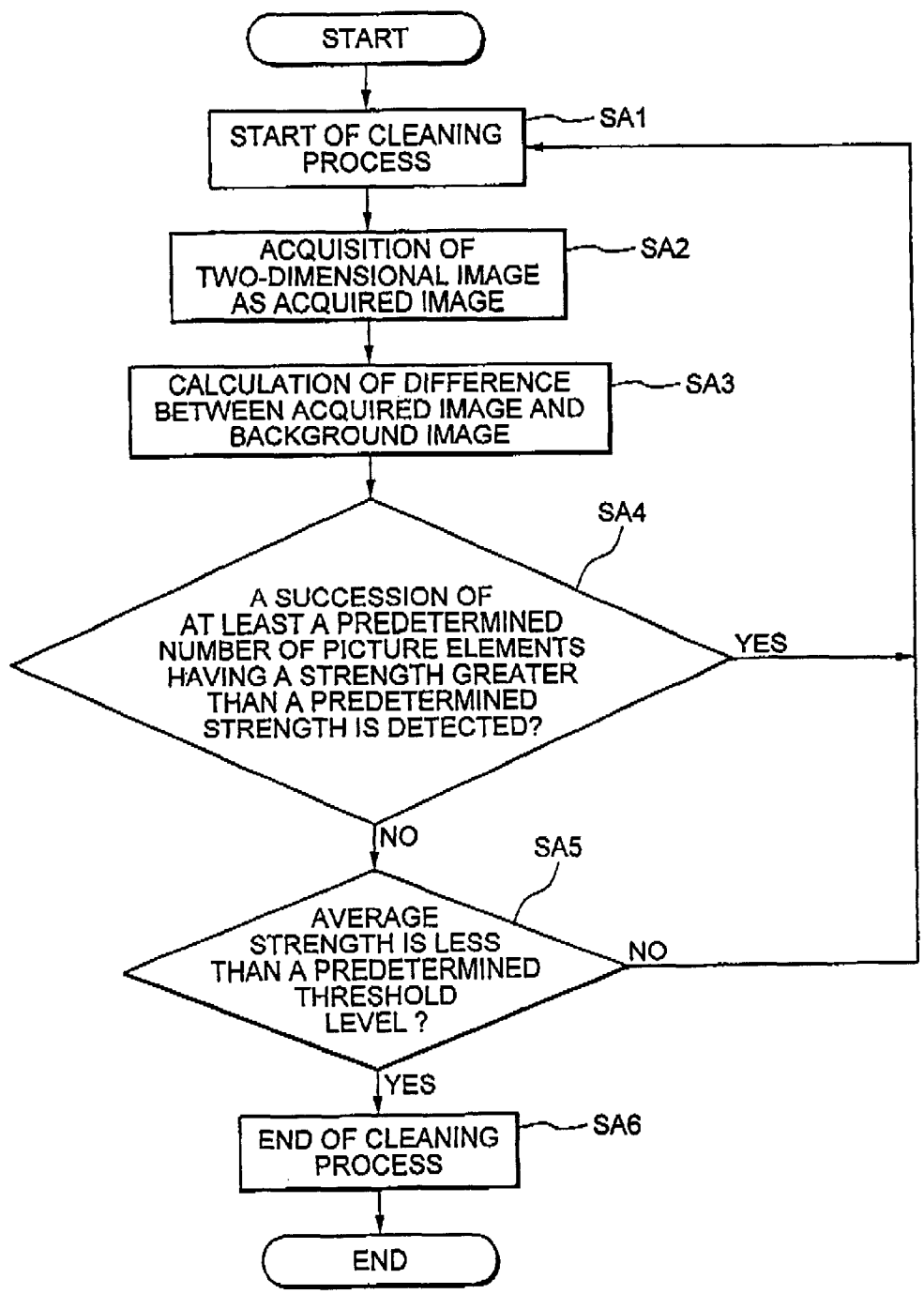
FIG. 4 is a flow chart for describing a cleaning end point detecting method according to this invention.

Referring to FIGS. 1 and 4, a third embodiment of this invention will be described.

Referring to FIG. 4, a method of detecting the end point of the cleaning process will be described.

During the cleaning process, the contamination is reduced in thickness. When the contamination is detached due to internal stress as the detached particles, the detached particles are discharged together with the cleaning gas. The detached particles have a size between several tens of nanometers and several micrometers and can be detected by an existing particle counter. The particle leaving the locus in FIG. 3 is a detached particle. On the other hand, a resultant gas as a product of the reaction between the cleaning gas and the contamination reacts in a gas phase to form a cluster of fine particles. The fine particles in the cluster are smaller in size than the detached particles and have a size of several tens of nanometers or less. Although not so great as to leave a locus, the fine particles in the cluster are present at a high density. Therefore, by adjusting the sensitivity of the CCD camera as the scattered beam monitoring (or measuring) unit 7, the cluster is observed as a cloud having an indefinite contour as illustrated in FIG. 2 or 3.

The contamination discharged by the cleaning process is not constant in size and the detached particles having a size of several hundreds of nanometers may not be produced. In view of the above, the detection of the end point can be more accurately carried out if the cluster cloud is relied upon.

Referring to FIG. 4, description will be made of the image processing using a background difference technique. Specifically, a clean vacuum chamber is preliminarily filled with the cleaning gas at a processing pressure. The laser beam is introduced into the vacuum chamber and a background image is picked up. Then, the cleaning process is started (step SA1) and the two-dimensional image is acquired as an acquired image (step SA2). The background image is subtracted from the acquired image to calculate the strength of an irradiated part irradiated by the laser beam (step SA3). Next, judgment is made about presence or absence of a succession of at least a predetermined number of picture elements having a strength greater than a predetermined strength (step SA4). Specifically, in presence of a succession of seven or more picture elements having a strength of 15 counts or more (yes in step SA4), presence of the particle or the cluster cloud is judged. Therefore, the cleaning process is continued (step SA1). On the other hand, in case of absence of the succession of seven or more picture elements having a strength of 15 counts or more (no in step SA4), judgment is made about whether or not the average strength is less than a predetermined threshold level which is equal to 7 counts (step SA5). Specifically, when the average strength is less than 7 counts (yes in step SA5), the completion of the cleaning process is judged (step SA6).

Fourth Embodiment

Figure 5:
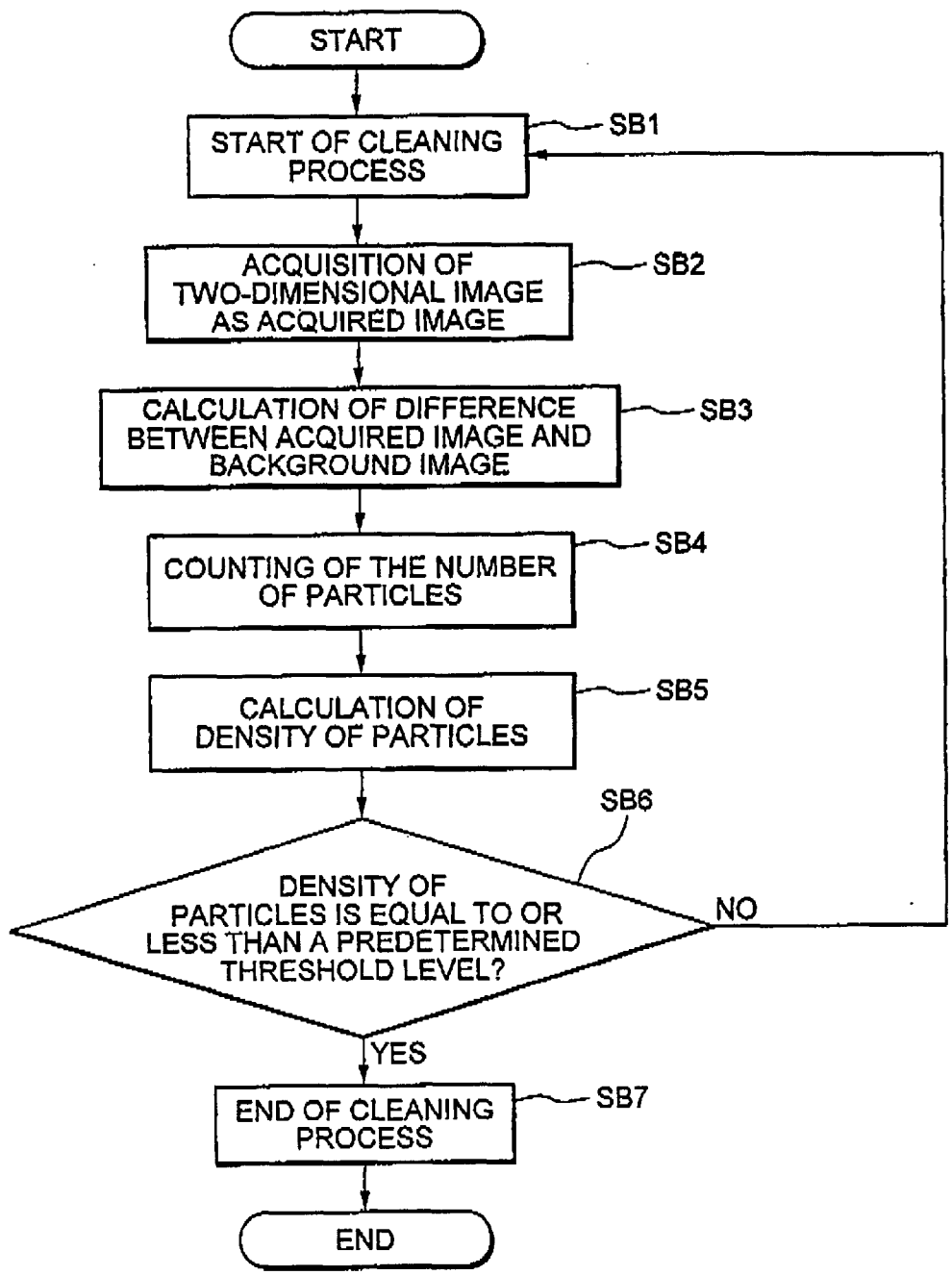
FIG. 5 is a flow chart for describing another cleaning end point detecting method according to this invention.

Referring to FIGS. 1 and 5, a fourth embodiment of this invention will be described.

In FIG. 5, detection of the end point of the cleaning process is carried out in a manner different from that described in conjunction with FIG. 4.

In the cleaning process for the tungsten thermal CVD apparatus using $ClF_3$ as the cleaning gas, it is presumed from the intensity of the image that the detached particles have a size on the order of several hundreds of nanometers. On the other hand, the fine particles in the cluster cloud produced in a vapor phase reaction is presumed to have a size of 20 nm or less from a preselected sensitivity.

Taking the sensitivity of the CCD camera (the scattered beam monitoring or measuring unit 7) and the intensity of the laser beam into consideration, the apparatus is adjusted to have a sensitivity such that those particles having a size of several nanometers can be detected.

In this embodiment, the end point of the cleaning process is detected also by the use of the background difference technique. Specifically, the clean vacuum chamber is preliminarily filled with the cleaning gas at the processing pressure. The laser beam is introduced into the vacuum chamber and the background image is picked up. Then, the cleaning process is started (step SB1) and the two-dimensional image is acquired as the acquired image (step SB2). The background image is subtracted from the acquired image to calculate the strength of the irradiated part irradiated by the laser beam (step SB3). Next, the number of particles having a size of 10 nm is counted (step SB4). The number of particles is divided by a preselected irradiation volume to calculate a volume density (step SB5). Next, judgment is made about whether or not the density is equal to or less than a preselected threshold level (step SB6). When the density is equal to or less than the preselected theshold level, for example, $100/cm^2$ (yes in step SB6), the completion of the cleaning process is judged (step SB7).

As described above, with the cleaning end point detection method and the cleaning end point detection apparatus according to this invention, the scattered beam scattered by the cluster cloud and the detached particles produced in the vacuum chamber is monitored as the two-dimensional image to be analyzed for the strength. In this manner, the end point of the cleaning process can be accurately detected.

The cleaning end point detection method and the cleaning end point detection apparatus of this invention are also applicable to an apparatus which does not use the plasma without changing the process.

The cleaning end point detection apparatus of this invention can be mounted to any desired position, such as a neighborhood of the inner wall of the vacuum chamber, for which the completion of the cleaning process is to be confirmed. With the apparatus of this invention, it is easy to monitor the state at a position which can not be reached by the plasma beam.

What is claimed is:

1. A cleaning end point detecting apparatus for detecting an end point of a cleaning process in which contamination attached to an inner wall of a reaction chamber (1) is removed by introducing a cleaning gas into said reaction chamber to produce within said reaction chamber a cluster cloud resulting from reacting part of said contamination with said cleaning gas and to detach the other part of said contamination from said inner wall as detached particles and by discharging said cluster cloud and said detached particles from said reaction chamber together with said cleaning gas, said apparatus comprising:

irradiating means (5) for irradiating a laser beam onto said cluster cloud and said detached particles within said reaction chamber to produce a scattered laser beam scattered by said cluster cloud and said detached particles;

monitoring means (7) for monitoring said scattered laser beam as two-dimensional image information; and judging means (3) for judging said end point of the cleaning process on the basis of said two-dimensional image information.

wherein said judging means judges, as said end point of the cleaning process, a time instant when not only said detached particles but also said cluster cloud is no longer detected on the basis of said two-dimensional image information.

2. A cleaning end point detection apparatus as claimed in claim 1, wherein said judging means judges, as said end point of the cleaning process, a time instant when a density of predetermined-sized particles having a predetermined size is decreased to a predetermined density, said predetermined size being substantially equal to a particle size of said cluster cloud.

3. A cleaning end point detection apparatus as claimed in claim 2, wherein said predetermined size is not greater than 20 nm.

4. A cleaning end point detection apparatus as claimed in claim 2, wherein said monitoring means comprises a CCD (Charge Coupled Device) camera.

5. A cleaning end point detection method of detecting an end point of a cleaning process in which contamination attached to an inner wall of a reaction chamber (1) is removed by introducing a cleaning gas into said reaction chamber to produce within said reaction chamber a cluster cloud resulting from reacting a part of said contamination with said cleaning gas and to detach the other part of said contamination from said inner wall as detached particles and by discharging said cluster cloud and said detached particles from said reaction chamber together with said cleaning gas, said method comprising the steps of:

irradiating a laser beam onto said cluster cloud and said detached particles within said reaction chamber to produce a scattered laser beam scattered by said cluster cloud and said detached particles;

monitoring said scattered laser beam as a two-dimensional image information; and judging said end point of the cleaning process on the basis of said two-dimensional image information.

6. A cleaning end point detecting method as claimed in claim 5, wherein said judging step judges, as said end point of the cleaning process, a time instant when not only said detached particles but also said cluster cloud is no longer detected on the basis of said two-dimensional image information.

7. A cleaning end point detection method as claimed in claim 6, wherein said judging step judges, as said end point of the cleaning process, a time instant when a density of predetermined-sized particles having a predetermined size is decreased to a predetermined density, said predetermined size being substantially equal to a particle size of said cluster cloud.

8. A cleaning end point detection method as claimed in claim 7, wherein said predetermined size is not greater than 20 nm.

* * * * *